US00PP23109P3

(12) United States Plant Patent
Harris

(10) Patent No.: US PP23,109 P3
(45) Date of Patent: Oct. 16, 2012

(54) AZALEA PLANT NAMED 'MNIHAR017'

(50) Latin Name: ***Rhododendron* sp.**
Varietal Denomination: MNIHAR017

(75) Inventor: James O. Harris, Lawrenceville, GA (US); Ella Ruth Harris, legal representative, Lawrenceville, GA (US)

(73) Assignee: Ella Ruth Harris, Lawrenceville, GA (US), Executor of the Estate of James O. Harris ( * ) Notice: Subject to any disclaimer, the term of this patent is extended or adjusted under 35 U.S.C. 154(b) by 135 days.

(21) Appl. No.: 12/807,057

(22) Filed: Aug. 25, 2010

(65) Prior Publication Data

US 2012/0054934 P1 Mar. 1, 2012

(51) Int. Cl.
*A01H 5/00* (2006.01)

(52) U.S. Cl. ..... Plt./240

(58) Field of Classification Search ..... Plt./240
See application file for complete search history.

*Primary Examiner* — June Hwu

(74) *Attorney, Agent, or Firm* — Jondle & Associates, P.C.

(57) ABSTRACT

A new and distinct variety of Azalea plant with spring and fall blooming, attractive, showy, single dark-red flowers, easily propagated by semi-hardwood cuttings in late spring through summer, moderate growth rate under normal fertilization and moisture conditions; broadly-rounded and freely-branching in habit, grows well in containers, thrives in shade or sun and is hardy in Zone 7, is disclosed.

2 Drawing Sheets

Genus and species: *Rhododendron* sp.
Variety denomination: 'MNIHAR017'.

BACKGROUND OF THE NEW PLANT

The present invention is a new and distinct variety of evergreen Azalea of the genus *Rhododendron*. This new Azalea, hereinafter referred to as 'MNIHAR017', was discovered in 2003 in Lawrenceville, Ga. 'MNIHAR017' originated from a planned cross hybridization in 1999 between the female azalea plant 'Conleb' (U.S. Plant Pat. No. 10,581) and the male azalea plant 'Jay Valentine' (unpatented) in a controlled environment in Lawrenceville, Ga. The present invention has a unique combination of blooming period, growth habit, and cold hardiness.

The new plant was first propagated via semi-hardwood cuttings in 2003 in Dearing, Ga. and has been asexually reproduced repeatedly by semi-hardwood cuttings in Dearing, Ga. for over seven years. The new plant retains its distinctive characteristics and reproduces true to type in successive asexual propagations by semi-hardwood cuttings.

Plant Breeder's Rights for the instant plant have not been applied for. 'MNIHAR017' has not been made publicly available or sold more than one year prior to the filing date of this application.

SUMMARY OF THE INVENTION

The following are the most outstanding and distinguishing characteristics of this new plant when grown under normal horticultural practices in Dearing, Ga.

1. Spring and fall blooming;
2. Attractive, showy, dark-red flowers;
3. Numerous single flowers;
4. Easily propagated by semi-hardwood cuttings in late spring through summer;
5. Moderate growth rate under normal fertilization and moisture conditions;
6. Upright, globose, dense and compact in nature;

7. Grows well in containers;
8. Thrives in shade or sun; and
9. Hardy in Zone 7.

DESCRIPTION OF THE PHOTOGRAPHS

This new Azalea plant is illustrated by the accompanying photographs which show buds, flowers, immature foliage and mature foliage. The colors shown are as true as can be reasonably obtained by conventional photographic means. The photographs are of 4-years-old plants grown in filtered shade in September in 2009 in Dearing, Ga.

DETAILED BOTANICAL DESCRIPTION OF THE NEW PLANT

Figure 1:
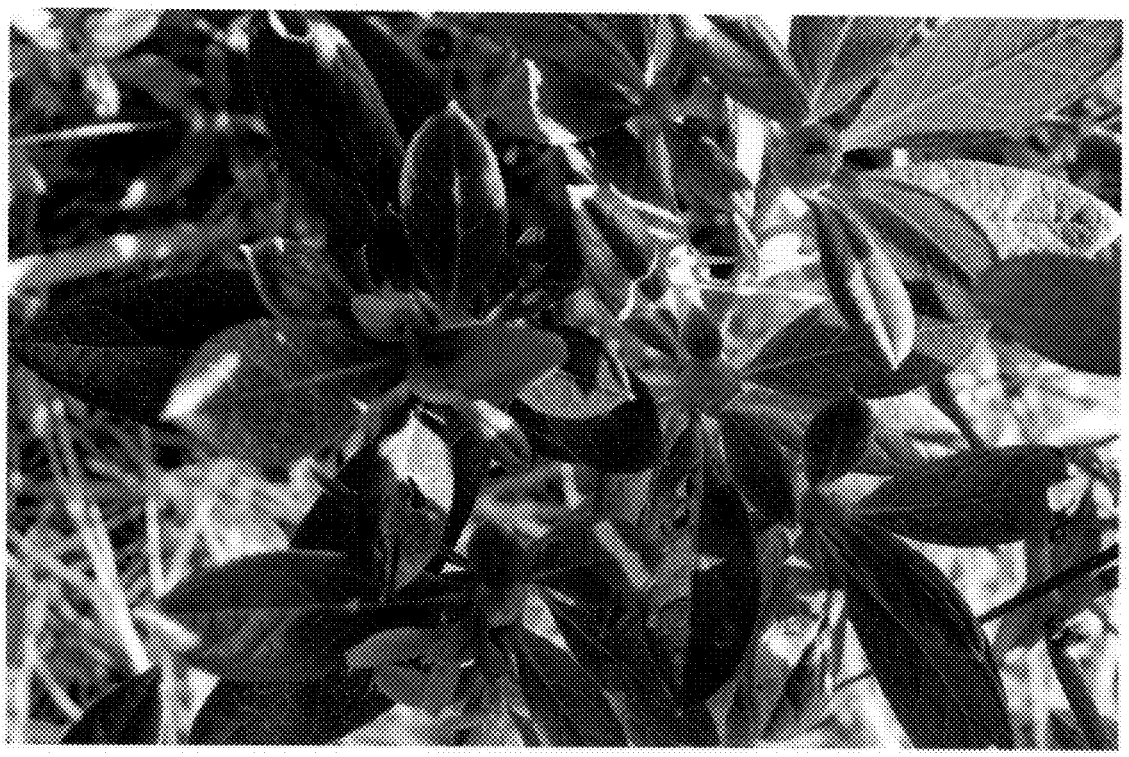
FIG. 1 is a close-up showing the stems and mature foliage.
Figure 2:
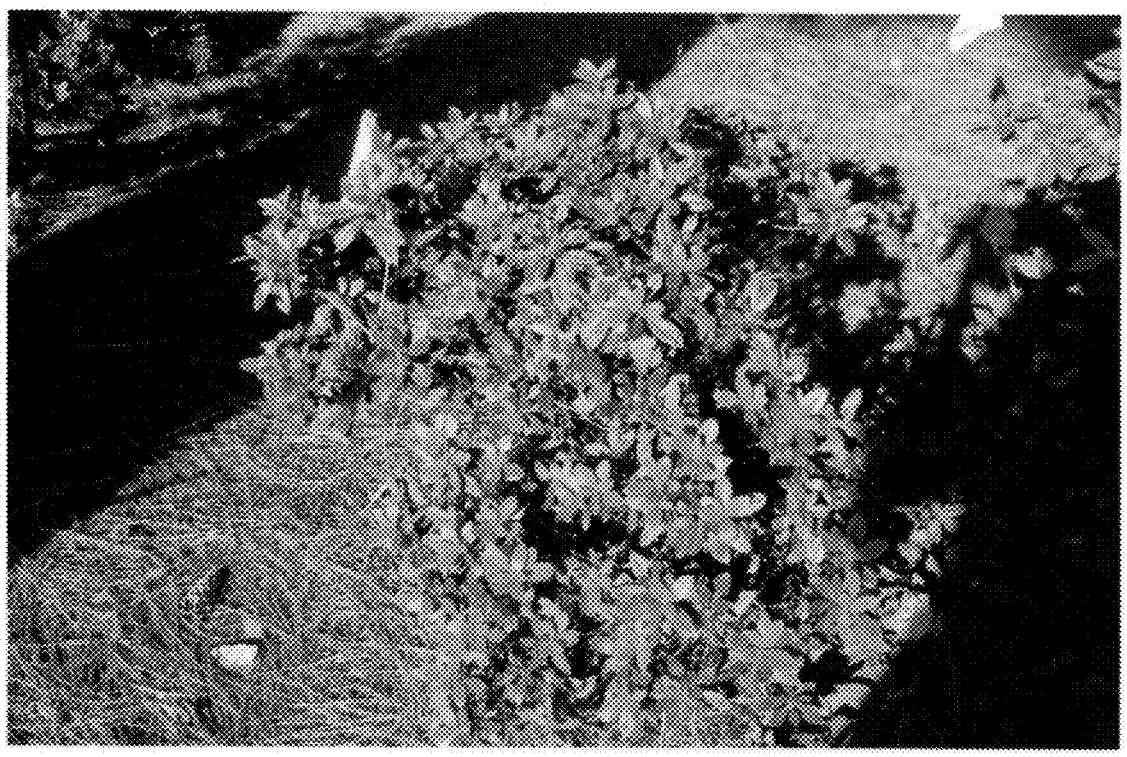
FIG. 2 shows the mature foliage and growth habit of a five-year-old plant.
Figure 3:
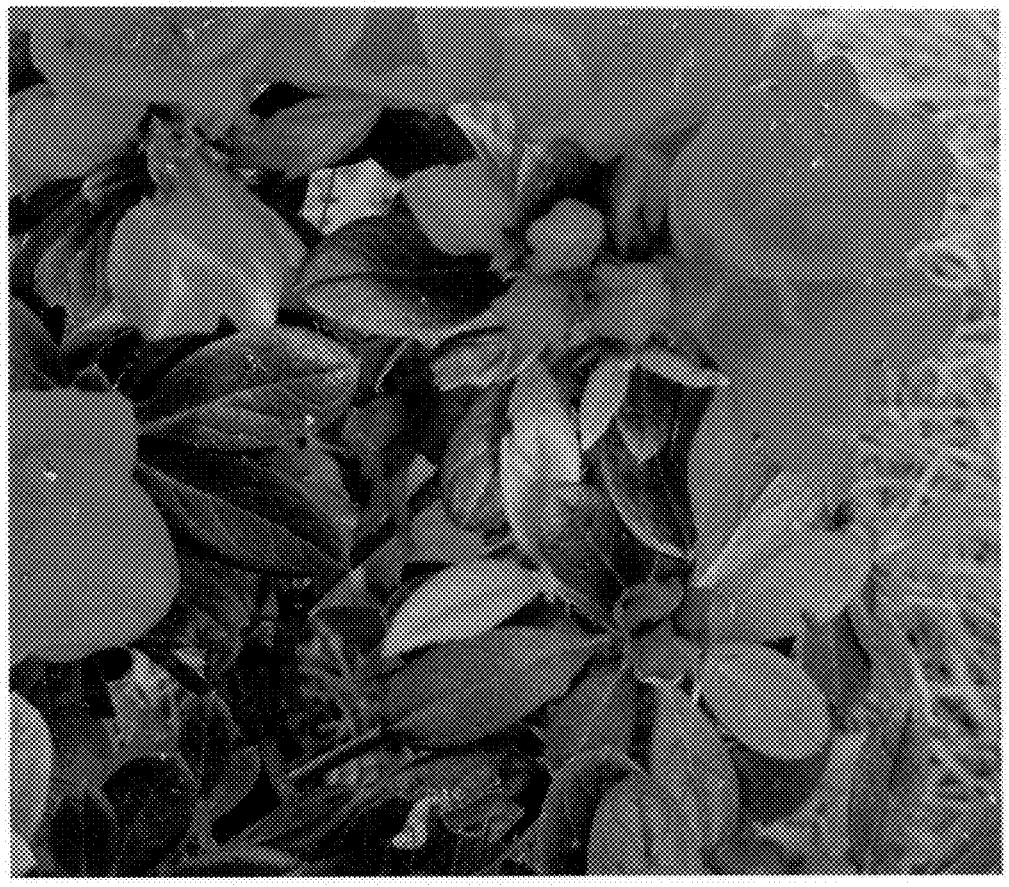
FIG. 3 is a close-up showing flower buds and immature foliage.
Figure 4:
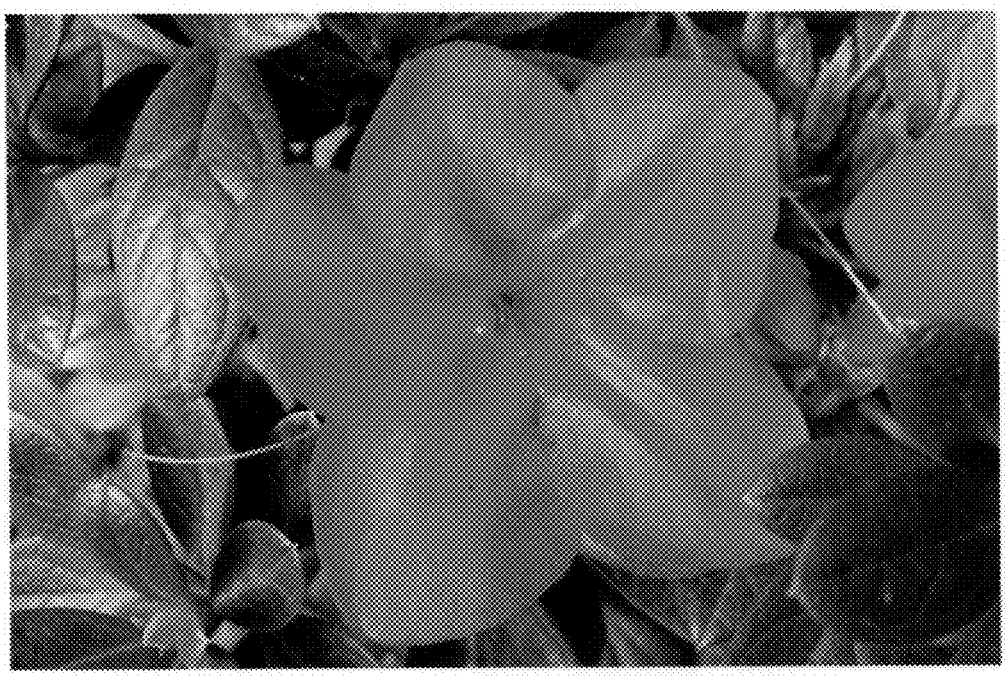
FIG. 4 is a close-up showing flower size, form, and color.

The following is a detailed description of the new variety of Azalea based on observations made of 4-year-old plants grown in 3-gallon containers according to wholesale commercial production conditions under full-sun and in an evaluation bed under semi-shade conditions in Dearing, Ga. in spring, summer, and fall in 2009. The colors of the various plant parts are detailed with reference to The Royal Horticultural Society Colour Chart (2001).

Classification:

*Family.*—Ericaceae.
*Species.*—*Rhododendron* sp.
*Common name.*—Azalea.
*Commercial name.*—'MNIHAR017'.

Parentage:

*Female parent.*—The azalea plant 'Conleb' (U.S. Plant Pat. No. 10,581).

*Male parent.*—The azalea plant 'Jay Valentine' (unpatented).

Growth:

*Form.*—Upright, globose.

*Texture.*—Medium.

*Height.*—91.44 cm to 121.92 cm.

*Width.*—137.16 cm to 167.64 cm.

*Growth habit.*—Freely-branching; dense and compact in nature.

*Growth rate.*—Moderate to rapid growth rate under normal fertilization and moisture conditions. In a period of five years from a rooted cutting the plant reaches a height of 60.96 cm and a spread of 83.82 cm. The growth rate is normally averages about 11.1 cm per year; the plant reaches a height of 91.44 cm to 121.92 cm at maturity while maintaining a dense habit due to the abundant branch development.

*Spring growth.*—The date of initial spring growth is April 5, followed by continuous growth through fall.

*Life cycle.*—Perennial and evergreen.

Leaves:

*Arrangement.*—Alternate, simple, and evergreen.

*Shape.*—Elliptic to obovate.

*Apex.*—Acuminate to slightly apiculate.

*Base.*—Acute.

*Margin.*—Entire.

*Length.*—3.5 cm.

*Width.*—1.3 cm.

*Venation pattern.*—Pinnate; the mid-veins and laterals are impressed on the upper surface and the prominent on the lower surface.

*Venation color* (*both upper and lower surfaces*).—RHS 146C (yellow-green).

*Immature leaf.*—Upper surface: Color: Matte, RHS 144A (yellow-green). Pubescence: Scabrous with some strigose along midrib and margin; color is RHS N155A (white). Lower surface: Color: Matte, RHS 146C (yellow-green). Pubescence: Strigose and scabrous along midrib and margin; color is RHS N155A (white).

*Mature leaf.*—Upper surface: Color: Semi-glossy, RHS 147A (yellow-green). Pubescence: Scabrous, color is RHS 166D (greyed-orange). Lower surface: Color: Matte, RHS 146B (yellow-green). Pubescence: Scabrous, strigose along midrib; color is RHS 164A (greyed-orange).

*Petiole.*—Length: 0.6 cm. Diameter: 0.15 cm by 0.1 cm. Pubescence: Strigose with some pilose, length is 0.1 cm to 0.3 cm; color is RHS 165C (greyed-orange) and RHS N155A (white) maturing to RHS 155C (white). Color: Begins as RHS 145A (yellow-green) and matures to RHS 146C (yellow-green).

Stems:

*Form.*—Densely branched at buds.

*Young stems* (1-*year old and younger*).—Color: RHS 46A (red) maturing to RHS 144A (yellow-green). Pubescence: Strigose RHS 155C (white) to RHS N167B (greyed-orange).

*Second-year stems.*—Stem and pubescence color: RHS 199B (greyed-brown) with a low amount of strigose pubescence present, RHS 199B (greyed-brown) in color. Length: 7 cm on average. Diameter: 0.15 cm. Pith: Solid and uniform. Internode length: Average 0.9 cm.

Flower buds:

*Arrangement and form.*—Tight; borne in groups of two or three, sheathed by a pair of modified leaf bracts which are 1.5 cm in length, 0.8 cm in width, persistent and RHS 147A (yellow-green) in color.

*Shape.*—Ovate.

*Apex.*—Acute.

*Base.*—Rounded.

*Length* (*at tight bud*).—1.3 cm.

*Diameter* (*at tight bud*).—0.6 cm.

*Color* (*of scales*).—Immature scales are RHS 145D (yellow-green) and mature to RHS 146B (yellow-green) with areas of RHS 178C (greyed-red).

*Texture.*—Pubescent; strigose pubescence RHS 165B (greyed-orange) in color.

*Pedicel.*—Length: 0.6 cm. Diameter: 0.2 cm. Texture: Pubescent, strigose pubescence that is RHS N155C (white). Color: RHS 46A (red).

*Calyx.*—Form and arrangement: Composed of 5 sepals in a cup-shape. Length: 0.9 cm. Width: 0.9 cm. Color: RHS 144A (yellow-green) with some RHS 46A (red) at base. Pubescence: Strigose and strigillose; RHS N155C (white) in color. Sepals: Shape: Lanceolate and broadly elliptical. Apex: Cuspidate to Obtuse. Base: Fused; joined at base to form a cup. Margin: Entire with some lobulate. Color: Upper RHS 144A (yellow-green) with some RHS46A (red) at base, Lower RHS 144A (yellow-green) with areas of RHS 145B (yellow-green). Length: 1.1 cm. Width: 0.45 cm.

Flowers:

*Type.*—Perfect, Single flowers.

*Shape.*—Open funnel-shaped.

*Flowering habit and period.*—Borne on the current season's growth; two and a half weeks beginning in early April in Dearing, Ga.; flowering resumes in late August and continues until frost which can be as late as November or December.

*Lastingness of flowers on the plant.*—4 to 6 days in the sun; 4 to 7 days in the shade, flowers are self-cleaning.

*Fragrance.*—Absent.

*Diameter.*—5.0 cm.

*Depth.*—3.8 cm.

*Petals.*—Quantity per flower and arrangement: 5 imbricate petals that are fused at the base and remain fused up to 1.5 cm. Shape: Obovate. Apex: Rounded. Base: Fused. Margin: Entire to undulate. Texture (both upper and lower surfaces): Glabrous. Length (of petals without spots): 3.8 cm. Width (of petals without spots): 2.5 cm. Length (of petals with spots): 3.5 cm. Width (of petals with spots): 2.2 cm. Color: upper surfaces are RHS 46A (red) with areas of RHS N34A (orange-red); lower surfaces are RHS 46B (red) with areas of RHS N34A (orange-red) near the apex; the upper surface of the spots are RHS 187B (greyed-purple) and lower surface of spots are not visible.

Reproductive parts:

*Pistil.*—Quantity and form: Single, non-petaloid. Length: 3.2 cm. Diameter: 0.05 cm. Stigma: Color: RHS 46A (red). Diameter: 0.15 cm. Style color: RHS 47B (red). Ovary: Pubescent, Pilose RHS N155A (white), with 5 locules.

*Stamens.*—Number: 5 to 6 per flower; non-petaloid with some slightly petaloid. Length: 2.5 cm. Color: RHS 47B (red). Anther: RHS 187A (greyed-purple); 0.25 cm in length by 0.1 cm in width. Pollen: Abundant; RHS 155D (white).

Fruit:

*Maturity.*—The capsule matures in about 6 months in Dearing, Ga. and the fruit set is low and contains about 100-300 non-winged seeds.

*Length.*—0.6 cm.

*Width.*—0.5 cm.

*Color.*—RHS 146B (yellow-green).

CULTURE

'MNIHAR017' grows well in a wide range of conditions and tolerates sun to shade. 'MNIHAR017' prefers moist, well-drained soil that is rich in organic matter and responds well to mulching and medium applications of fertilizer. 'MNIHAR017' does best in soil with a pH of 5.0 to 5.5 and is propagated with semi-hardwood cuttings in late spring through the summer. Azaleas root in five to six weeks with high 80% plus percentage of rooting, tissue culture is also an effective means of propagation for azaleas.

DISEASES AND INSECTS

Lace bugs, root weevils, and spider mites can be a problem. Fungal and bacterial pathogens have not been observed, but no resistance testing has been performed and no claim to abnormal resistance to pathogens can be made.

COMPARISON WITH PARENTAL AND COMMERCIAL VARIETIES

In Table 1, the 'MNIHAR017' is compared to parental varieties 'Conleb' (U.S. Plant Pat. No. 10,581) and 'Jay Valentine' (unpatented) and lists the differences between the varieties.

TABLE 1

| Characteristic | 'MNIHAR017' | 'Conleb' | 'Jay Valentine' |
|---|---|---|---|
| Plant Height (Mature) | 91.44 cm to 121.92 cm | 121.92 cm to 152.4 cm | 121.92 cm |
| Flower Diameter | 5 cm | 6.5 cm | 6.25 cm to 7.62 cm |
| Flower Form | Single | Single to semi-double | Single |
| Flower Color | Dark Red | Red | Deep Red |
| Bloom Period | April and late August until frost | April and late July until frost | April |
| Hardy Zone | 7 | 7 | 7 |
| Stamen Number | 5 to 6 | 0 to 9 | 5 |
| Stamen Type | Non-petaloid with some slightly petaloid | Petaloid and Non-petaloid | Petaloid |

When 'MNIHAR017' is compared to the commercial variety 'Roblen' (U.S. Plant Pat. No. 16,248), 'MNIHAR017' has a broader growth habit (60.96 cm and a spread of 83.82 cm in five years) than 'Roblen' which has a height of 91.44 cm and a spread of 60.96 cm in six years. Additionally, 'MNIHAR017' produces dark-red flowers, while 'Roblen' has bright red flowers.

I claim:

1. A new variety of Azalea plant named 'MNIHAR017' as herein shown and described.

* * * * *